(12) United States Patent
Verleun

(10) Patent No.: US 11,926,650 B2
(45) Date of Patent: Mar. 12, 2024

(54) METHOD FOR CASCADED PROCESSING OF FRESH ALGAE

(71) Applicant: SABIDOS B.V., Otterlo (NL)

(72) Inventor: Theodorus Verleun, Otterlo (NL)

(73) Assignee: SABIDOS B.V., Otterlo (NL)

( * ) Notice: Subject to any disclaimer, the term of this patent is extended or adjusted under 35 U.S.C. 154(b) by 350 days.

(21) Appl. No.: 16/771,069

(22) PCT Filed: Dec. 13, 2018

(86) PCT No.: PCT/EP2018/084690
§ 371 (c)(1),
(2) Date: Jun. 9, 2020

(87) PCT Pub. No.: WO2019/115672
PCT Pub. Date: Jun. 20, 2019

(65) Prior Publication Data
US 2021/0198326 A1 Jul. 1, 2021

(30) Foreign Application Priority Data
Dec. 15, 2017 (EP) .................................... 17207640

(51) Int. Cl.
*C12N 13/00* (2006.01)
*A23J 1/00* (2006.01)
(Continued)

(52) U.S. Cl.
CPC ............. *C07K 14/405* (2013.01); *A23J 1/006* (2013.01); *A23L 17/60* (2016.08); *A23L 17/65* (2016.08);
(Continued)

(58) Field of Classification Search
CPC ....... C07K 14/405; A23L 17/60; A23L 17/65; A23L 27/60; A23J 1/006; C12N 13/00; A21D 13/80; A21D 2/264
(Continued)

(56) References Cited

U.S. PATENT DOCUMENTS

2017/0119018 A1* 5/2017 Lei ........................... A21D 2/36

FOREIGN PATENT DOCUMENTS

| CN | 103771918 A | 5/2014 |
|---|---|---|
| CN | 104672325 A | 6/2015 |
| JP | 63-83170 A | 4/1988 |
| JP | 2005-245443 A | 9/2005 |

OTHER PUBLICATIONS

Postma, P. R. et al. J. Appl. Phycol. 30: 1281-12-93 (Year: 2017).*
(Continued)

*Primary Examiner* — Hamid R Badr
(74) *Attorney, Agent, or Firm* — BROWDY AND NEIMARK, PLLC

(57) ABSTRACT

The present invention relates to a method for processing fresh algae at ambient temperature by subjecting algae to an osmotic shock and treating the disrupted algae with an enzyme composition comprising cell wall degrading enzymes. This gentle process at ambient temperature allows for the isolation of algal protein which has good solubility, also in the presence of salt and good foaming, emulsifying and water binding properties. Another advantage is that this method of protein isolation allows for cascaded biorefinery, since protein isolation may be followed by a treatment of the remaining biomass with carbohydrate degrading enzymes to produce clean biogas in high yields and a mineral rich water stream in anaerobic digestion.

9 Claims, 1 Drawing Sheet

(51) Int. Cl.
  *A23L 17/00* (2016.01)
  *A23L 17/60* (2016.01)
  *C07K 14/405* (2006.01)
  *A21D 2/26* (2006.01)
  *A21D 13/80* (2017.01)
  *A23L 27/60* (2016.01)

(52) U.S. Cl.
  CPC .............. *C12N 13/00* (2013.01); *A21D 2/264* (2013.01); *A21D 13/80* (2017.01); *A23L 27/60* (2016.08); *A23V 2002/00* (2013.01)

(58) Field of Classification Search
  USPC ............................................ 435/68, 81, 68.1
  See application file for complete search history.

(56) References Cited

OTHER PUBLICATIONS

Ventura, M. R. et al. Small Ruminant Research. 29: 325-327 (Year: 1998).*

Vilg J. V. et al: "PH-driven solubilization and isoelectric precipitation of proteins from the brown seaweed Saccharina latissima- effects of osmotic shock. water volume and temperature". Journal of Applied Phycology, pp. 585-593, vol. 29, No. 1 (Sep. 2016).

Postma PR et al. "Biorefinery of the macroalgae Ulva lactuca: extraction of proteins and carbohydrates by mild disintegration", Journal of Applied Phycology, pp. 1281-1293, vol. 30, No. 2 (Oct. 2017).

H. K. Maehre et al., "Enzymatic Pre-Treatment Increases the Protein Bioaccessibility and Extractability in Dulse (Palmaria palmata)" Marine Drugs, p. 196, vol. 14, No. 11 (Oct. 2016).

P. A. Harnedy et al., "Extraction of protein from the macroalga Palmaria palmata", LWT- Food Science and Technology, pp. 375-382, vol. 51, No. 1 (Apr. 2013).

Geng et al., Process technologies and chemical-physical properties of seaweed extracts as well as their application in agriculture, Chinese Journal of Ecology 36(10):2951-2960 (2017) with English asbtract.

Dillehay et al., Monte verde: seaweed, food, medicine, and the peopling of South America, Science 320:784-786 (2008).

* cited by examiner

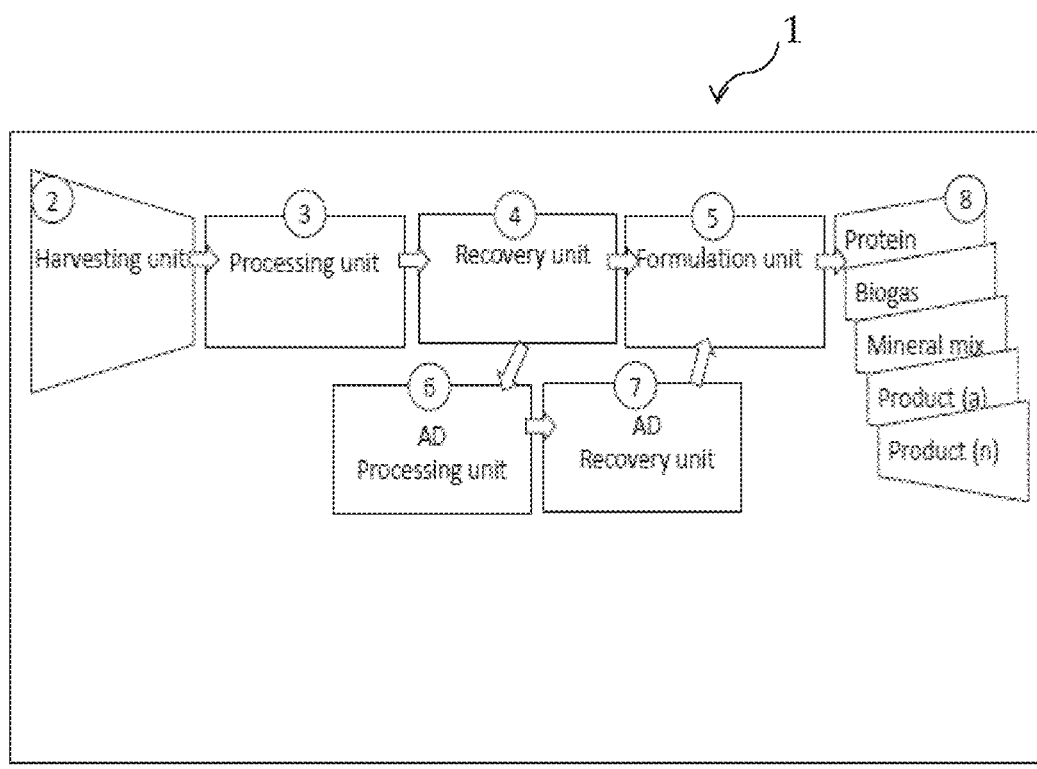

METHOD FOR CASCADED PROCESSING OF FRESH ALGAE

FIELD OF THE INVENTION

The present invention relates to a method for processing algae to recover algal protein and biogas. The invention also relates to the protein recovered by the process.

BACKGROUND OF THE INVENTION

Algae are a valuable source of polysaccharides, proteins, minerals and oils. To isolate these valuable constituent from algae, algae need to be processed. Fresh water algae may be harvested and processed locally. For salt water algae, the so-called seaweed, harvesting and processing take place at separate locations. The seaweed is harvested offshore, transported to the main land and then processed onshore. By the time processing is started, decomposition or deterioration of the seaweed has started. As a consequence, the algae cannot be used for food, pharma or cosmetic applications anymore, unless after intensive processing or using substantial amounts of anti-microbial preservation agents. In addition, a lot of water is transported while bringing the algae onshore, which is very heavy and costly.

Alternatively, algae are harvested offshore and also preserved offshore to extend storage or shelf life before processing. The preserved seaweed is then transported onshore for further processing. This avoids the transportation of a lot of water, but does not avoid damage to the algal constituents like protein. Preservation is frequently in the form of drying or freezing. Vilg & Undeland (2017) J. Appl. Phycol. 29:585 describes the extraction of protein from frozen or freeze-dried seaweed. Postma et al J Appl Phycol (2018) 30:1281 is a study of different protein extraction methods from dried seaweed. Maehre et al. 2016 March drugs 14:196 describes an optimised alkaline protein extraction from dried seaweed. Harnedy & FitzGerald 2013 Food Sci technol 51:375 describes another optimized alkaline protein extraction from oven-dried *Palmaria palmate*. Preservation, and in particular the heat used for drying the seaweed, may lead to protein deformation or denaturation and thus to a decrease in functionality and associated value reduction. In addition, heating for drying large amounts of wet algal biomass requires substantial amount of (costly) energy. Another disadvantage is that preservatives are typically added to the algal biomass. These preservatives may end up in the final food product or in case of acid (ensiling) treatments will also destroy algal constituents, which is undesirable.

It would be desirable to have a more efficient, a more economical and a more gentle method for seaweed processing which yields a good quality functional, typically intact, protein product which can be used in food applications and which allows for further value extraction from the remaining biomass after protein isolation.

SHORT DESCRIPTION OF THE FIGURE

FIG. 1 One embodiment of a device according to the invention, comprising a harvesting and washing unit 2; a processing unit 3 for enzymatic digestion, a recovery unit 4 for isolation and concentration of the protein, an anaerobic digestion processing unit 6, a recovery unit 7 for recovery of the products from 6 and a formulation unit 5 for formulation of the products 8 from recovery units 4 or 7.

DETAILED DESCRIPTION OF THE INVENTION

In one aspect, the present invention relates to a method for processing algae. The method comprises (i) subjecting algae to an osmotic shock; (ii) treating the shocked algae with an enzyme composition comprising cell wall degrading enzymes; (iii) separating the enzyme treated algae into a solid phase and a liquid phase, wherein the enzyme treatment of the algae is started within three hours after harvesting and the temperature in step (i) to step (iii) is in the range of 4 to 30 degrees C.

In conventional industry, if harvesting and processing take place at different sites, the biomass is typically transported from the site of harvesting to the site of processing. In the method according to the present invention, instead of taking the harvested biomass to the processing site, the processing plant is taken to the site where the biomass is harvested in order to process the biomass as fresh as possible, to yield the highest functional value of the constituents. In the method according to the present invention, algae are processed at or very close to the site of harvesting. This is particularly advantageous if algae are harvested at another site than the main processing site, e.g. offshore, which is typically the case for marine algae, also referred to as seaweed or macro-algae. Using the process of the invention, there is little chance of decomposition or deterioration of the algae before the processing has started. High costs for water transportations to bring e.g. seaweeds to a processing plant (seaweeds consist for more than 90% w/w of water) are also avoided. Therefore, proteins obtained from the algae are also of good quality, showing functional properties, for example of good solubility, may be produced more economically and may be used for food applications.

Another advantage of the method according to the invention is that after the extraction of the protein, the remaining biomass may be used for further value extraction. For example, the biomass may be used for production of biogas or for recovery of minerals. In one embodiment according to the invention, the biomass remaining after the extraction of the protein is exposed to a carbohydrase enzyme mix in order to release sugars. The carbohydrate rich hydrolysed biomass is then fed into an anaerobic digester to yield biogas and a mineral rich water stream. The latter may be used as or in a fertilizer composition, which is also part of the invention. From this carbohydrate rich fraction also other food constituents may be retrieved, such as for example sugars, alginates, carrageenan and fucoidan.

Although the method is very advantageous for processing marine algae, the method may be used for any type of algae processing, be it on shore or offshore. In one embodiment, the method is used for offshore processing of algae, in particular seaweed or macro-algae, into protein, optionally followed by further producing biogas or fertilizer composition from the algal biomass remaining after protein recovery. The term "biogas" refers to the product of anaerobic digestion or anaerobic fermentation of biomass. Biogas comprises primarily methane and carbon dioxide and may have small amounts of hydrogen sulphide, moisture and siloxanes.

The method of the invention is particularly advantageous when harvesting biomass, such as algae, in a situation where processing site and harvesting site are apart, because the method allows for immediate processing of the biomass. Processing is typically started quickly to minimize the time the algae are exposed to air or oxygen, such as within 30 minutes, within 60 minutes, within 90 minutes, within 2 hours, within 2.5 hours or within 3 hours from harvesting.

The term "processing" in the present context refers to a process which includes the disruption of algal cells or the treatment of algal biomass with cell wall degrading enzymes. Just drying the algal biomass without further disruption of the cells or without enzyme treatment is not regarded as the start of processing.

In the context of the present invention, "offshore" refers to a marine or fresh water location, such as in a sea, ocean, estuary, river or lake, the coast or river bank. In one embodiment, the marine or fresh water location is at least 1 km off the shore, coast or river bank, such as between 1 and 200 km, between 1 and 50 km or between 50 and 200 km, off the shore, coast or river bank. Offshore does not refer to ponds or raceways on land.

Since the temperature during processing never exceeds 30 degrees C. and is preferably between 4 and 30 degrees C., between 5 and 25 degrees C. or between 15 and 25 degrees C., the protein which is isolated from algae is not subjected to deformation or denaturation and retains its functional properties, such as for example its solubility. Using the method according to the invention, dried or concentrated liquid algal protein may be obtained.

Fresh algae are used in the method according to the invention. In the context of the present invention, "fresh algae" refers to algae as harvested, without further processing such as drying and freezing. Therefore the term "fresh algae" does not include dried, powdered, rehydrated, frozen, ensiled or thawed algae. Fresh algae typically have a water content in the range of between 80 and 95% w/w. Freshly harvested algae are harvested less than four hours ago, such as three hours ago, two hours ago or one hour ago.

Apart from algae, the harvest may include small marine sea life or other solids, such as plastic, which are preferably removed before processing the algae. The algae may constitute from between 86% to 100% w/w of the sea life in the harvest. In a preferred embodiment, the algae constitute 90% to 100% w/w or 99% to 100% w/w of the sea life in the harvest. Harvesting refers to separating algae from the surrounding water, such as recovering algae from marine or fresh water location, such as a lake, river or sea, estuary or ocean. Algae may be harvested by any suitable means, for example by collecting free floating algae or by cutting or stripping the algal biomass from nets and ropes on which they were seeded and grown out of. In one embodiment, algae or seaweed are seeded on cultivation ropes. Harvesting then comprises stripping algae or seaweed from the ropes.

From within 30 minutes to two or three hours after harvesting the algae from a marine or fresh water location, the algae are subjected to an osmotic shock which leads to disruption of the algae and to liberation of the cell contents. The osmotic shock may liberate the cell contents partly or completely. The osmotic shock may disrupt all algal cells or part of the algal cells, such as for example at least 50%, at least 60% or at least 75% of the algal cells. The osmotic shock may be effected by any suitable means, such as by using water, as long as the temperature never exceeds 30 degrees C. The temperature during osmotic shock is preferably between 4 and 30 degrees C., between 5 and 25 degrees C. or between 15 and 25 degrees C. In one embodiment, demineralised water is used to give seaweeds an osmotic shock. The demineralised water is preferably used in a ratio of algae:water of 1:1 to 1:10, based on the weight of the wet algae. The osmotic shock treatment typically last from 5 to 60 minutes, preferably from 5 to 20 minutes.

Before they are subjected to the osmotic shock, the algae may be sized into small pieces for example by cutting or slicing them or putting them in a blender or cutter. In one embodiment, the algae are sized into small pieces in demineralised water, which means that they are sized into small pieces while they are subjected to the osmotic shock.

Directly or almost directly after harvest, and before they are subjected to an osmotic shock, the algae may be washed to remove small sea life, such as fish, crustaceans and crabs, and to remove debris, such as plastic, drift wood or buoys. For washing, for example excess sea water of a temperature between 4 and 30 degrees C. may be used.

Directly or almost directly after harvest, and before they are subjected to an osmotic shock, adhering sea water may be removed. Adhering sea water may be removed by low speed centrifugation in order not to damage the algae. In one embodiment, adhering sea water is removed by centrifugation at 100-500 rpm, preferably at 100 to 200 rpm or 200-300 rpm.

In the context of the present invention, the term "algae" refers to a group of unicellular or multicellular photosynthetic eukaryotic non-vascular aquatic organisms which live in or under sea, brackish water or fresh water and which contain diverse bioactive compounds which are used in agriculture, the cosmetic industry, the food or feed industry or in the pharmaceutical industry. In particular seaweeds are rich in polysaccharides showing antimicrobial, antioxidant or antiviral activities. Seaweeds contain valuable molecules, such as proteins, vitamins, spore elements, polyphenols, iodine, alginic acid and derivatives, carrageenans, chlorophylls, carotenoids and agar. The method according to the invention may be used to process algae, in particular marine algae, also referred to as seaweed or macro-algae, such as red algae (Rhodophyta), green algae (Chlorophyta) and brown algae (Ochrophyta, Phaeophyceae). Algae which may be used in the method according to the invention include but are not limited to *Alaria* species, *Ascophyllum* species, *Caulerpa* species, *Chondrus* species, *Durvillaea* species, *Enteromorpha* species, *Fucus* species, *Gracilaria* species, *Laminara* species, *Pelvetia* species, *Pyropia* species, *Porphyra* species, *Sargassum* species, *Saccharina* species, *Ulva* species and *Undaria* species. Of particular interest are *Ascophyllum nodosum, Chondrus crispus, Enteromorpha intestinalis, Fucus spiralis, Fucus vesiculosus, Gracilaria bursa-pastoris, Gracilaria crassa, Gracilaria dura, Gracilaria longa, Gracilaria verrucosa, Laminaria digitata, Laminaria ochroleuca, Laminaria pallida, Lessonia nigrescens, Macrocystis integrifolia, Macrocystis pyrifera, Nemacystus decipiens, Nereocystis luetkeana, Palmaria palmata, Porphyra purpurea, Porphyra umbilicalis, Saccharina japonica, Saccharina latissima, Saccharina longicruris, Saccharina sessilis, Sargassum filipendula, Sargassum fusiforme, Sargassum muticum, Ulva intestinalis, Ulva compressa, Ulva lactuca* and *Undaria pinantifida*. In one embodiment, one or more of the above species or a combination of two or more of the mentioned species are processed in the method according to the invention. In a preferred embodiment, green algae are processed, in particular *Ulva* species, more in particular *Ulva lactuca*.

Within two to three hours after harvesting, the ruptured algal biomass is treated with a composition comprising cell wall degrading enzymes. The composition is used to release proteins connected or associated with other cell mass, such as cell walls and cell organelles. In one embodiment, the enzyme composition comprises at least 0.10% w/w of cell wall degrading enzymes based on the total weight of the enzyme composition, for example 0.10% w/w to 100% w/w, 0.20% w/w to 95% w/w, 0.50% w/w to 90% w/w, 1.0% w/w to 90% w/w, 1.0% w/w to 10% w/w, 1.0% w/w to 20% w/w, 10% w/w to 20% w/w, 20% w/w to 65% w/w, 70% w/w to 95% w/w or 80% w/w to 95% w/w, all based on the total weight of the enzyme composition. In another embodiment, the enzyme composition consists of cell wall degrading enzymes.

Suitable cell wall degrading enzymes which may be present in the enzyme composition include but are not limited to cellulases (EC 3.2.1.4), xylanases (EC 3.2.1.8 and EC 3.2.1.32), beta-glucanases (EC 3.2.1.6), amylases (EC 3.2.1.1 and EC 3.2.1.2), phytases (EC 3.1.3.8 and EC 3.1.3.26), phospholipases (PLA1, PLA2, PLB, PLC, PLD, EC 3.1.1.4, EC 3.1.4.11 and EC 3.1.4.4) and polygalacturonases (EC 3.2.1.15). In one embodiment, the cell wall degrading enzyme is the main activity in the enzyme composition, in another embodiment the cell wall degrading enzyme is a side or minor activity in the enzyme composition. The enzyme composition comprises one or more of these cell wall degrading enzymes. The skilled person will understand that the optimal mixture of enzymes may vary between types of algae and seasons. Therefore, any mixture of cell wall degrading enzymes may be used as long as it is used on fresh or freshly harvested algae. In one embodiment, the ruptured algae is treated with an enzyme composition comprising a combination of a cellulase, an endo-xylanase, a beta-glucanase, an alpha-amylase, a beta-amylases, a phytase, a polygalacturonase and a phospholipase PLA2. In another embodiment, the ruptured algal biomass is treated with an enzyme composition comprising a phytase (EC 3.1.3.8) and a phospholipase (PLA1, PLA2, PLB, PLC, PLD, EC 3.1.1.4, EC 3.1.4.11 and EC 3.1.4.4). In another embodiment, the ruptured algal biomass is treated with an enzyme composition comprising an endo-xylanase (EC 3.2.1.8) and a phospholipase (PLA1, PLA2, PLB, PLC, PLD, EC 3.1.1.4, EC 3.1.4.11 and EC 3.1.4.4). In one embodiment, an enzyme composition is used which comprises enzymes with an activity towards cellulose, xylan, beta-glucan, amylase, phytate, pectin, galacturonic acid or phospholipids. In another embodiment, an enzyme composition is used which comprises beta-glucanase, phytase, poly-galacturonase and phospholipase. In another embodiment an enzyme composition is used which comprises polygalacturonase with an activity of at least 20 000 AVJP/g; endo 1, 3 beta glucanase with an activity of at least 80 BGLU/g; fungal beta glucanase with an activity of at least 100 000 BGF/g; bacterial amylase with an activity of at least 7500 U/g; phytase with an activity of at least 5000 FTU/g; phospholipase A2, and a xylanase. Prior to use these enzymes are mixed in a ratio of 1:1:1:1:1:1 and the mix is dosed at 500 ml per 1000 kg 100% dry matter biomass. These enzymes are commercially available, for example from DSM, Delft, the Netherlands.

The cell wall degrading enzymes in the enzyme composition may be obtained by isolation, such as from a plant, fungi of bacteria, by de novo synthesis or by mutagenesis of a known enzyme.

The cell wall degrading enzymes are used to release part or all intracellular proteins, including those connected or associated with other cell mass. In one embodiment, at least 30% w/w, at least 40% w/w, at least 50% w/w, at least 60% w/w, at least 70% w/w, at least 80% w/w, at least 90% w/w, such as between 30% w/w and 60% w/w, between 45% w/w and 70% w/w or between 50% and 90% w/w of the intracellular protein is released.

Any suitable dosage of enzyme preparation may be used. In one embodiment, 0.001% w/w to 5% w/w, 0.005% w/w to 2% w/w or 0.01% w/w to 1% w/w cell wall degrading enzyme composition is used per 1000 kg 100% dry matter biomass. The dry matter content of the algae may be determined by any method known in the art and typically comprises removing all of the moisture in a sample of the algae or algae by evaporation of water, for example by drying a representative sample of algae in an oven and weighing the sample before and after drying.

Depending on the enzyme dosage, it may take from about 5 minutes to 50 hours, from 30 minutes to 48 hours, from 6 hours to 24 hours, from 18 hours to 30 hours or from 30 hours to 50 hours to make part or all intracellular proteins available. In one embodiment, the ruptured algal biomass is enzyme treated for 24 hours to 48 hours. During enzyme treatment the temperature does not exceed 30 degrees C. and is preferably between 4 and 30 degrees C., between 5 and 25 degrees C. or between 15 and 25 degrees C.

There is no need to adjust the pH in any of the steps of the process. The pH as is is used and is typically in the range of pH 5.5 to pH 7.5, for example pH 6.0 to 7.5.

After enzyme treatment, solids and liquid phase are separated (step (iii)), preferably by centrifugation or filtration. Using centrifugation, a pellet and a protein containing supernatant are obtained. Using filtration, a retentate and a protein containing filtrate are obtained.

The protein may be recovered from the supernatant or the filtrate, typically by concentration. Concentration may be by any suitable means such as by ultrafiltration, centrifugation, precipitation or nano-filtration, as long as the temperature does not exceed 30 degrees C. and is preferably between 4 and 30 degrees C., between 5 and 25 degrees C. or between 15 and 25 degrees C. The concentrated protein may be stored until use. The concentrated protein may easily be transported to another location, for example to the shore if harvesting and processing took place off-shore. The protein which is isolated from fresh algae has better functionality than commercial algal proteins, which are frequently prepared from dried algae, and may be used in known applications for proteins or algal proteins, such as in the food industry, in the feed industry, in the cosmetic industry or in the pharmaceutical industry, for example as a foaming agent, gelling agent, thickener, emulsifier, colourant, pigment, anti-oxidant or anti-microbial agent.

Optionally, the protein is dried, onshore or off-shore, preferably by an instant drying method, such as spray drying. In one embodiment, the protein is instantly dried by spray drying using a box dryer (Sanovo technology A/S, Odense, Denmark). Suitable conditions for box drying are for example an inlet temperature in the range of 175 to 185 degrees C. and an outlet temperature in the range of 90 to 97 degrees C. The protein may be concentrated before or during drying.

Using the method according to the invention, protein may be obtained in high yields, such as for example a yield of at least 65% w/w, at least 70% w/w, at least 75% w/w, at least 80% w/w, at least 85% w/w or at least 90% w/w, based on total protein in fresh algae, may be obtained.

The solid phase obtained in step (iii) after separation off the protein, for example pellet or retentate, contains carbohydrates, including sugars, fats, oils and minerals. The carbohydrates, which are the main constituents of the solid phase, may be used for the production of renewable energy, such as biogas, bio-ethanol or bioplastic. The minerals may be used as a fertilizer. The fats and oils may be used for feed, food, cosmetic or pharmaceutical application. After the extraction of protein, the remaining biomass may thus be used for further value extraction.

Many suitable methods for producing biogas from biomass by anaerobic digestion have been published, such as one-stage processes, using one reactor, and two-stage processes, using two reactors, both processes including the steps of (a) hydrolysis and acidification and (b) acetogenesis or methanogenesis. In two stage processes, step (a) and (b) are performed in separate reactors or compartments. These steps may both be performed microbially. Alternatively, step (a) is performed enzymatically, using an enzyme preparation, and step (b) is performed microbially, for example as described in WO2013/000928. In a preferred embodiment for biogas production, the solid phase remaining after protein extraction is subjected to a two-stage process and first subjected to an enzyme treatment before microbial digestion by methanogenic organisms. Suitable carbohydrate degrading enzymes which may be present in the enzyme composition include but are not limited to amylases (EC 3.2.1.1 and EC 3.2.1.2), glucose oxidase (EC 1.1.3.4), cellulases (EC 3.2.1.4), xylanases (EC 3.2.1.8 and EC 3.2.1.32), beta-glucanases (EC 3.2.1.6), phytases (EC 3.1.3.8 and EC 3.1.3.26), phospholipases (PLA1, PLA2, PLB, PLC, PLD, EC 3.1.1.4, EC 3.1.4.11 and EC 3.1.4.4) and polygalacturonases (EC 3.2.1.15). The enzyme composition may comprise one or more carbohydrate degrading enzymes. The skilled person will understand that the optimal mixture of enzymes may vary between types of algae and seasons. Therefore, any mixture of carbohydrate degrading enzymes may be used as long as it is used on the biomass obtained after protein extraction from fresh or freshly harvested algae. In one embodiment, the cell carbohydrate degrading enzyme is the main activity in the enzyme composition, in another embodiment the carbohydrate degrading enzyme is a side or minor activity in the enzyme composition. All enzymes are commercially available, for example from DSM, Delft, the Netherlands. Any suitable dosage of enzyme preparation may be used. In one embodiment, an enzyme mixture comprising a cellulose with an activity of at least 3500 CMC U/g, a glucanase with an activity of at least 100 000 BGF/g, a xylanase with an activity of at least 120 000 \AVJP/g and a phytase with an activity of at least 5000 FTU/g is used, preferably comprising the enzymes in a weight ratio of 1:2:2:1 and the mix dosed at 0.05 ml per kg wet weight biomass after protein extraction.

Preferably, enzymatic hydrolysis of the carbohydrates and microbial digestion takes place in separate reactors or separate compartments. Any suitable reactor configuration may be used for biogas production according to the invention, for example a continuously stirred tank reactor (CSTR), a sequential batch reactor (SBR) or an anaerobic membrane bioreactor (AnMBR). Preferably, more sophisticated systems are used such as upflow anaerobic sludge blanket (UASB) or expended granular sludge bed (EGSB).

Producing biogas from fresh algae from which the protein fraction has first been removed is very advantageous, because it may lead to higher yields of biogas and to cleaner biogas which contains less nitrogenous impurities, in comparison to conventional biogas processes in which protein has not been removed before enzymatic treatment. Biogas yields may be in the order of 250 to 600 Nm3, such as 300 to 500 Nm3 or 400 to 500 Nm3 biogas/1000 kg 100% dry weight algae at 60% to 80%, such as 70% methane after about 12 hours residence time. In one embodiment, 460 Nm3 biogas/1000 kg 100% dry weight seaweed at 70% methane was produced at 12 hours residence time.

Clean biogas produced from fresh seaweed after removal of most or all of the algal protein is therefore another aspect of the invention. The skilled person will understand that protein may or may not be extracted from the protein containing liquid phase after separating off the solid phase for biogas production. In any case clean biogas will be obtained. In one embodiment, the invention therefore relates to a method of
(i) subjecting algae to an osmotic shock;
(ii) treating the shocked algae with an enzyme composition comprising cell wall degrading enzymes;
(iii) separating the enzyme treated algae into a solid phase and a liquid phase, wherein the enzyme treatment of the algae is started within three hours after harvesting and the temperature in step (i) to step (iii) is in the range of 4 to 30 degrees C.
(iv) using the solid phase obtained in step (iii) for producing biogas, preferably by enzymatic hydrolysis using carbohydrate degrading enzymes followed by microbial methanogenesis,
(v) optionally, recovering protein from the liquid phase obtained in step (iii).

The biogas is preferably produced by a two stage process which comprises enzymatic hydrolysis of the solid phase using a carbohydrase enzyme preparation followed by microbial methanogenesis. Alternatively, the solid phase may be converted into syngas using gasification processes known in the art.

In another aspect, the present invention relates to an algal protein preparation which is obtainable by a process according to the invention, i.e. from processing fresh algae. The algal protein preparation obtained from fresh algae will have good functional protein properties, such as for example solubility. Its solubility is typically better than, such as twice or three times, the solubility of protein prepared from preserved, such as dried, seaweed. In one embodiment, the protein preparation obtained from fresh algae has a solubility of at least 55% w/w at least 60% w/w, at least 65% w/w or at least 70% w/w, based on total protein brought into dispersion at a pH in the range of pH 3 to 10. The solubility is also good in the presence of NaCl and typically better than, such as three times or four times, the solubility of protein prepared from preserved, such as dried, seaweed. In one embodiment, the protein preparation obtained from fresh algae has a solubility of at least 55% w/w at least 60% w/w, at least 65% w/w, at least 70% w/w, at least 75% w/w or at least 80% w/w in the presence of NaCl, based on total protein brought into dispersion. In one embodiment, the protein according to the invention has a solubility of 1 mg/ml at any NaCl concentration in the range of 0.05 to 3% w/v NaCl. In one embodiment, the protein according to the invention has a solubility of at least 55% w/w at least 60% w/w, at least 65% w/w, at least 70% w/w, at least 75% w/w or at least 80% w/w at any pH in the range of pH 3 to 10 and a solubility of at least 55% w/w at least 60% w/w, at least 65% w/w, at least 70% w/w, at least 75% w/w or at least 80% w/w in the presence of 0.05 to 3% w/v NaCl. Solubility at different pH values or NaCl concentrations may for example be determined by dispersing a certain amount of dry product in demiwater, then setting the pH with phosphoric acid or sodium hydroxide, or then setting the salt concentrations with NaCl, and next centrifuging the dispersions/solutions. Solubilised protein may then be measured in the supernatant, for example by using a commercial kit, such as a Pierce™ BCA Protein Assay Kit (Thermo Scientific, Bleiswijk, the Netherlands) and measuring the absorption at 562 nm in a spectrometer. The protein may have an isoelectric point at a pH in the range of 7.5 to 8.5.

The skilled person will understand that the exact amino acid composition of the protein obtained may vary from seaweed type to seaweed type but the protein according to the invention may have high levels of asparagine or glutamine, for example at least 10% w/w or at least 15% w/w based on the weight of the total amino acids. It may also have substantial amounts of glycine, proline or alanine, for example at least 5% w/w, at least 7% w/w or at least 10% w/w based on the weight of the total amino acids.

The protein may also have good nutritive as well as functional properties, such as foaming, emulsifying or water binding properties, and may be used in many applications, in particular in food, pharma and cosmetic as well as feed applications.

In one embodiment, the invention relates to an algal protein or protein preparation which comprises two or more of the following characteristics:
a) comprising at least 10% w/w or at least 15% w/w asparagine or glutamine, based on the weight of the total amino acids;
b) comprising at least 5% w/w, at least 7% w/w or at least 10% w/w glycine, proline or alanine, based on the weight of the total amino acids;
c) comprising a solubility of at least 55% w/w at least 60% w/w, at least 65% w/w, at least 70% w/w, at least 75% w/w or at least 80% w/w at any pH in the range of pH 3 to 10;
d) a solubility of at least 55% w/w at least 60% w/w, at least 65% w/w, at least 70% w/w, at least 75% w/w or at least 80% w/w at any NaCl concentration in the range of 0.05 and 3% w/v NaCl;
e) comprising a solubility of at least 1 mg/ml at any NaCl concentration in the range of 0.05 and 3% w/v NaC;l
f) comprising an iso-electric point at a pH in the range of pH 7 to pH 9;
g) comprising emulsifying properties comparable to egg protein.

In one embodiment, an algal protein or protein preparation according to the invention has all these characteristics.

In another aspect, the present invention relates to a device 1 (FIG. 1) for processing algae according to the processing method of the invention. The device 1 is mobile and can therefore move to or be taken to the site of harvesting. The device comprises a harvesting unit 2 for harvesting, cleaning and washing; a processing unit 3 for enzymatic digestion of the harvest; and a recovery unit 4 for isolation and concentration of the protein. The device may optionally further comprise an anaerobic digestion processing unit 6, a recovery unit 7 for recovery and optionally concentration of the products from 6 and a formulation unit 5 for formulation of the products from recovery units 4 or 7. The device may comprise or be installed in, at, on or to a mobile unit which can be sailing or can be towed to places where algae flourish, grow or are farmed, for example to a ship, barge or vessel. In this way, algae may be harvested at a specific site where at a certain time of the year algae are present.

In one embodiment, the present invention relates to a method for processing algae, wherein the method comprises
(i) subjecting algae to an osmotic shock;
(ii) treating the shocked algae with an enzyme composition comprising cell wall degrading enzymes;
(iii) separating the enzyme treated algae into a solid phase and a liquid phase, wherein the enzyme treatment of the algae is started within three hours after harvesting, and the temperature in step (i) to (iii) is in the range of 4 to 30 degrees C.;
(iv) drying the liquid phase of step (iii) to obtain the protein, preferably by spray drying;
(v) optionally, using the solid phase obtained in step (iii) for producing biogas, bioplastic or bioethanol, wherein step (i) to step (v) are carried out offshore on a mobile device according to the invention.

The skilled person will understand that the above-mentioned embodiments may be combined to form new embodiments. Embodiments and preferred embodiments mentioned for the method of processing may also be applied to the products of the processing method according to the invention, such as the protein, the biogas, the mineral stream and the mobile device, and vice versa.

EXAMPLES

Materials & Methods
Enzyme Preparation A

The enzyme preparation used for releasing of the cell contents contained the following enzymes (all from DSM, Delft, the Netherlands, except otherwise indicated):
  2 ml cellulase (Filtrase BRX)
  2 ml xylanase (Filtrase NLC),
  2 ml amylase (MATS classic),
  2 ml phytase (Phytase 5000L),
  2 ml phospholipase A2 (Purifinae PLA2), and
  90 ml Demineralised water
  2 g beta-glucanase/endo xylanase (Battonage, Oenobrands, Montferrer-sur-lez, France) which was dissolved under gentle agitation in the earlier mentioned enzymes in liquid form.

For a diluted enzyme preparation, the enzyme preparation was diluted with demi water.

Example 1 Processing of Green Algae Using the Method According to the Invention

Fresh green algae (*Ulva Lactuca*, 5 kg) were harvested and washed using an excess of fresh sea water of a temperature of maximally 20 degrees C. Attached water was removed by low speed centrifugation. Then 5 liters of demineralised, chilled water was added and the mixture was chopped in a blender until pieces of approximately 1 sq mm were obtained. The sliced biomass was divided into two parts. To one part, the control, 25 ml demineralised water was added. The other part was incubated with 25 ml of a ten times diluted enzyme preparation A for release of the cell contents within one hour after harvesting.

Both parts were stirred for 24 hours at room temperature (actually <20 C) and then centrifuged at 4 degrees C., 4500 rpm for 10 minutes and the supernatant was collected. The pellet was resuspended in demineralised water, centrifuged again and the supernatant collected and added to the first supernatant. Collected supernatants were frozen until further analysis. Further analysis showed that the supernatant contained protein. This shows that protein can be isolated from algae using the gentle process according to the invention. The protein was dried by spray drying the supernatant and stored for further analysis.

Example 2 Processing of Red Algae Using the Method According to the Invention

Fresh red algae (*Gracillaria*, 5 kg) were harvested and washed using an excess of fresh sea water of a temperature of maximally 20 degrees C. Attached water was removed by low speed centrifugation and cut into pieces of approximately 1 sq. mm and further treated as described in Example 1, including enzyme treatment within two hours after harvesting. Collected supernatants were frozen until further analysis. Further analysis showed that the supernatant from

*Gracillaria* contained protein. Also another type of red algae, fresh *Chondrus*, were harvested and processed using the protocol as described in Example 1, including enzyme treatment within two hours after harvesting. Collected supernatants were frozen until further analysis. Further analysis showed that the supernatant from *Chondrus* contained protein. This shows that protein can be isolated from red algae using the gentle process according to the invention.

Example 3 Processing of Brown Algae Using the Method According to the Invention

Fresh brown algae (*Fucus*) were harvested and washed using an excess of fresh sea water of a temperature of maximally 20 degrees C. Attached water was removed by low speed centrifugation and algae cut into pieces of approximately 1 sq. mm and further treated as described in Example 1, including enzyme treatment within two hours after harvesting. Collected supernatants were frozen until further analysis. Further analysis showed that the supernatant contained protein. This example shows that the process according to the invention also may be used for protein isolation from brown algae.

Example 4 Large Scale Processing of Fresh *Ulva* for Isolation of Protein and Production of Biogas in a Cascaded Process Green algae (*Ulva lactuca*, 76 kg) were harvested and washed using an excess of fresh seawater of a temperature of maximum 20 degrees C. Attached water was removed by low speed centrifugation. Portions of 1 kg seaweed was mixed with 1 liter of demineralized water and chopped in a Robot Coupe Cutter R10 into pieces of approximately 1 sq. mm. With an additional 1 liter of demineralized water the chopped seaweed was put in a clean new 1000 liter IBC. The total 76 kg of *Ulva* was incubated for 24 hour with 600 liter of demineralised water under constant gentle agitation within three hours after harvest. At the beginning of the 24 hour incubation period enzyme preparation A (500 ml enzyme mix/1000 kg 100% dry matter biomass) was added. After the incubation period the remaining seaweed solids were removed by filtration of the total slurry over a 4 times folded cheese cloth. The liquid, protein containing fraction, filtrate going through the cheese cloth was collected and the protein was dried by spray drying the supernatant using a box dryer (Sanovo technology A/S, Odense, Denmark) with an inlet temperature of 180 degrees C. and an outlet temperature of 94 degrees C. The spray-dried protein was then characterized as described in the Examples below. The protein extraction efficiency for the method according to the invention is presented in Table 1 and was about 81% w/w based on dry weight and as percentage of total protein present in the starting material. Protein was measured using the BCA assay (Thermo Scientific, Bleiswijk, the Netherlands).

TABLE 1

| Starting material (fresh Ulva) | Extraction efficiency | Yield (GOA product) |
|---|---|---|
| 76 Kg seaweed | | |
| 14% w/w dry matter | | |
| 10.6 Kg dry matter | | 4.5 Kg protein rich powder produced |
| 12% Of dry matter is protein | | 23% Protein |
| 1.28 Kg protein present | 81% w/w | 1.04 Kg protein produced |

The retained solids, in the cheese cloth, were then re-incubated for 48 hours with carbohydrase enzyme preparation comprising cellulase Methaplus L100 (>3500 CMC U/g)/glucanase; Axiase 100 (>120000 AVJP/g)/xylanase; Filtrase NLC (>100000 BGF/g) and phytase; Maxamyl P (>5000 FTu/g) in a weight ratio of 1:2:2:1 (all enzymes from DSM. Delft, the Netherlands) and dosed at 0.05 ml (mix) per kg wet weight biomass after protein extraction, in order to hydrolyze as much as possible the carbohydrates into solution. These hydrolyzed solids were transferred to an anaerobic digester (EGSB-skid of Hydrothane) for production of biogas and mineral rich water stream, which mineral stream may be used as a fertilizer. The biogas conversion showed there was no need for pH stabilizers nor for additional nutrients and at a residence time of 12 hours a result of 460 Nm3 biogas/1000 kg 100% dry weight seaweed at 70% methane could be achieved. This is a much higher yield than could be expected when an all microbial process was used, i.e. without enzymatic treatment, or when total seaweeds were used, without first extracting protein.

Example 5 SDS Page Analysis of the GOA Protein Isolated According to the Method of the Invention The spray-dried protein obtained in Example 4 was analysed using SDS-PAGE. Electrophoresis was performed according to Laemmli (1970) Nature 227:5259. A protein sample which was obtained from *Ulva* after drying the seaweed with hot air, grinding it into flakes and storing it for eight weeks before isolating protein (Hello Seaweed, Fuzhou Beautiful Agricultural development Co, China) was taken as a reference. For SDS-PAGE analysis, both samples were exposed to fresh water. The dried seaweed sample got few hours of rehydration time and the GOA sample got same amount of time to re-dissolve, both under gentle agitation. After centrifugation, the pellet was discarded and the supernatant containing the protein was recovered. An aliquot from each sample was pipetted from the supernatant, then diluted with extraction buffer (1.5% SDS, 20% glycerol and 0.01% bromophenol blue) to similar protein concentration. The gel protein bands were developed in a fast-stain ready-to-use gel (SERVA electrophoresis GmbH, Germany). Gel analysis was done with freeware: GelAnalyzer 2010. A marker set of 6 kDa-67 kDa was used. SDS-PAGE analysis showed that the GOA protein sample, obtained from fresh *Ulva* seaweed, contains more proteins with a molecular size larger than 40 kDa than the *Ulva* reference sample obtained from dried material. The GOA sample has almost twice the amount of 27-30 kDa protein and contains less protein with a size smaller 6 kDa range (Table 2). These results indicate that the protein sample obtained from fresh seaweed contains more intact protein and less degraded protein than the sample from dried seaweed. More intact protein also means more functional protein. Degradation of protein is detrimental to functional properties such as emulsification, viscosity and heat-set gelling.

TABLE 2

| kDa area | GOA-protein profile (ex-fresh Ulva) | Protein profile (ex dried Ulva) | Ratio Fresh vs dried material |
|---|---|---|---|
| 58-62 | 2.5% | — | N.A |
| 50-55 | 9.5% | 8% | 1.2 |
| 40-45 | 14% | 7.5% | 1.9 |
| 27-30 | 71% | 39% | 1.8 |
| 18-22 | — | 18.5% | N.A |
| <6 | 3% | 27% | 0.1 |

Example 6 Amino Acid Composition of the Protein Sample According to the Invention The amino acid composition of the spray dried protein sample of Example 4 was determined by acid hydrolysis and HPLC and is presented in Table 3. The protein contained high levels of asparagine (15% of total amino acids) and glutamine (20% of amino acids), as well as substantial amounts of glycine, proline and alanine

TABLE 3

| Amino acid | g/kg | % of total |
|---|---|---|
| Tryptophan | | |
| Alanine | 17.4 | 10.5 |
| Arginine | 4.3 | 2.6 |
| Asparagine | 25.1 | 15.1 |
| Cysteine | 2.7 | 1.6 |
| Glutamine | 34.1 | 20.6 |
| Glycine | 12.5 | 7.5 |
| Hydroxyproline | 1.8 | 1.1 |
| Histidine | 1.7 | 1.0 |
| Isoleucine | 6.3 | 3.8 |
| Leucine | 6.6 | 4.0 |
| Lysine | 5.0 | 3.0 |
| Methionine | 2.1 | 1.3 |
| Phenylalanine | 6.9 | 4.2 |
| Proline | 10.0 | 6.0 |
| Serine | 5.9 | 3.6 |
| Threonine | 6.5 | 3.9 |
| Tyrosine | 5.9 | 3.6 |
| Valine | 10.9 | 6.6 |
| TOTAL | 165.7 | 100% |

Example 7 Protein Solubility at Different pH Values

To analyse protein solubility of a spray-dried protein sample obtained in Example 4 (GOA sample), 1 g dry product of the GOA protein sample was dispersed in 100 ml demiwater. A sample obtained from dried and milled *Ulva* was run in the same experiment. Of the *Ulva* sample, 2 g dry *Ulva*/100 ml demi-water was used in order to have comparable amount of protein load in the test. Dispersions were set at pH 3, 4, 4.5, 5, 6, 7, 8, 9 with phosphoric acid (low pH) and sodium hydroxide (high pH). Then, the dispersions/solutions were centrifuged. A 100 microliter aliquot was pipetted from the supernatants in the respective test tubes and diluted to a concentration range suitable for soluble protein analysis with a Pierce™ BCA Protein Assay Kit (Thermo Scientific, Bleiswijk, the Netherlands) using a Shimadzu UV/VIS spectrometer at 562 nm. The measured protein mg/ml is then corrected for the used sample weight and dilution factor in the BCA assay. The solubility of the seaweed proteins showed little variation and was relatively constant. Table 4 is a comparison of the solubilities of *Ulva* and GOA proteins and clearly shows that the solubility of the GOA protein sample is 3 to 12 times higher than the solubility of the *Ulva* reference sample. The average protein solubility is 5 times higher for the GOA protein sample. The results also show a variability of 38% for *Ulva* versus a variability of just 5% for GOA, indicating that *Ulva* is much more sensitive to pH than GOA, with *Ulva* showing a minimum solubility at pH 6. This means that isolating protein from fresh seaweed allows for the preparation of a protein sample with much higher solubility and which is much more constant over the whole pH range than a protein sample from dried seaweed.

TABLE 4

| pH | % soluble protein from dried Ulva | % soluble protein from fresh GOA | ratio fresh/dried |
|---|---|---|---|
| 3 | 22-24 | 75-77 | 3.3 |
| 4 | 16-18 | 78-80 | 4.6 |
| 4.5 | 13-15 | 73-76 | 5.3 |
| 5 | 16-18 | 76-77 | 4.5 |
| 6 | 5-7 | 73-74 | 12.1 |
| 7 | 11-13 | 72-73 | 6.0 |
| 8 | 18-19 | 66-69 | 3.7 |
| 9 | 26-28 | 75-77 | 2.8 |

The results presented also indicate different iso-electric points for the three protein samples. A dip in solubility is indicative of an iso-electric point. In this way, the iso-electric point for the GOA sample around pH 8 and for the *Ulva* reference sample around pH 6. These results indicate that isolating protein from fresh seaweed leads to a protein with a different iso-electric point and thus a different pH behavior in application.

TABLE 5

| sample | estimated iso-electric point (pH) |
|---|---|
| Egg albumin | 4.5 |
| Ulva dried | 6 |
| GOA sample invention | 8 |

Example 8 Salt Sensitivity of the Protein Sample from Fresh Seaweed

To analyse protein solubility in the presence of different concentrations of NaCl, 1 g of a spray-dried protein sample obtained in Example 4 (GOA sample) was dispersed in 100 ml demi-water. An egg albumin (EA) sample and a sample obtained from dried and milled *Ulva* were run in the same experiment a reference. Of the *Ulva* sample, 2 g was used in order to have comparable amount of protein load in the test. The solubilized proteins from GOA, *Ulva* and EA were diluted in demi-water to diminish salt effects of the sample. The diluted samples were then set at NaCl concentrations of 0-3%. The protein solutions were centrifuged and 100 μl was pipetted from the supernatants of the respective samples for soluble protein analyses with a Pierce™ BCA Protein Assay Kit (Thermo Scientific, Bleijswijk, the Netherlands) using a Shimadzu UV/VIS spectrometer at 562 nm. The measured protein mg/mL was then corrected for the used sample weight and dilution factor in the BCA assay. Measurements were done in duplicate. At all salt concentrations, the GOA protein sample has much higher solubility than the *Ulva* sample. For *Ulva* on average 44±12 mg protein was soluble versus increasing salt percentages. For GOA 192±11 mg protein was soluble versus increasing salt percentages. Percentages solubility in the presence of NaCl are shown in Table 6. It can be noted that the average protein solubility is 4 times higher for GOA than for *Ulva*, and that the variability for *Ulva* is 27% versus a variability of just 6% for GOA, indicating that *Ulva* is more sensitive to changes in salt concentration. This shows that a protein sample obtained in accordance with the invention, from fresh seaweed, has higher solubility than protein samples form dried seaweed, which stability is not affected by high salt concentrations.

TABLE 6

| NaCl % | % soluble protein from dried Ulva | % soluble protein from fresh GOA | ratio fresh/dried |
|---|---|---|---|
| 0 | 20-20 | 77-79 | 3.9 |
| 0.1 | 25-27 | 83-85 | 3.2 |
| 0.5 | 20-21 | 74-75 | 3.6 |
| 1 | 11-13 | 69-70 | 5.8 |
| 1.5 | 28-29 | 80-82 | 2.8 |
| 2 | 15-15 | 76-77 | 5.1 |
| 2.5 | 20-21 | 77-79 | 3.8 |
| 3 | 18-19 | 72-74 | 4.0 |

Example 9 Preparation of Sponge Cake

Standard receipt (Italian cake version): 9 gram whole egg powder, 221 gram water, 210 gram sugar, 150 gram wheat flour and 75 gram of potato starch. The whole egg powder was replaced by proteins like soy, whey, sunflower or the GOA-protein according to the invention. The mixture was kneaded into a dough using a Hobart N50. The dough was cut in circles of 10 cm to form the cake. The dough was baked in an oven at 180 degrees C. for 22 minutes, until the cakes had a nice gold/yellow colour. The cakes were removed from the oven and allowed to cool. The cakes prepared from seaweed (GOA) protein had a very nice appearance, comparable to the cakes from whole egg protein. The (GOA) seaweed cakes maintained the round form and did not crumble, unlike the cakes from other proteins like soy, whey and sunflower protein which crumbled when touched or which had a very rough/uneven surface. This shows that for dough consistency and baking properties the GOA (seaweed) protein can be used as replacement of whole egg powder.

Example 10 Preparation of 75% Mayonnaise

Standard recipe (Sanovo egg group) was used; 15% egg yolk powder, 107 gram of water, 2 gram of salt 375 gram of (canola) oil and 10 gram of vinegar. All gently and in consecutive order added and mixed by using a speed mixer (Bosch 300W type 4179 or Hobart N50). The emulsion was stored for 24 hours at 2-5 degrees C. to stabilise. After 24 hours the viscosity was measured. For comparison the egg-yolk powder was replaced by GOA (seaweed) protein, soy, pea, sunflower proteins. Also mixes (50/50) whole egg powder/GOA (seaweed) protein were tested.

The mayonnaise from the seaweed (GOA) protein obtained in Example 4 was of good consistency. The soy protein—mayonnaise emulsion or pea protein—mayonnaise emulsion broke even before it was formed. This shows that the GOA protein has good emulsifying properties comparable to egg yolk. It also shows good scoopability and smearability of the GOA protein emulsion. The mixes of whole egg powder/GOA protein did not perform worse than the individual pure proteins.

The main observed difference for the GOA protein showed in the very low syneresis of the emulsion. The latter shows that GOA protein forms more stable emulsions compared to whole egg powder and clearly than the other tested emulsions of soy, pea or sunflower protein. After 4 weeks refrigerated storage at 2-5 degrees C., there was still no syneresis in the GOA (seaweed) protein emulsion, whereas all the others had become almost completely liquid. The experiment was stopped due to mold formation on all samples.

In conclusion, a) protein isolated by the method according to the invention allows for great emulsion formation; b) mixes of protein according to the invention and egg did not impair the properties of the emulsion; c) proteins according to the invention show a much lower syneresis than tested proteins like soy protein, whey protein, sunflower protein or pea protein, which offers new opportunities for the use of such emulsion in food applications.

The invention claimed is:

1. A method for processing seaweed, the method comprising:
    (i) subjecting fresh seaweed to an osmotic shock for 5 to 20 minutes;
    (ii) treating the shocked fresh seaweed with an enzyme composition comprising cell wall degrading enzymes;
    (iii) separating the enzyme treated seaweed into a solid phase and a liquid phase,
    wherein treating the shocked fresh seaweed with the enzyme composition is started within three hours of harvesting the seaweed and the temperature in step (i) to step (iii) is in the range of 4 to 30 degrees C., and wherein seaweed protein is obtained at a yield of at least 65% w/w, based on total protein in the seaweed.

2. The method according to claim 1, wherein steps (i) to (iii) of processing of the fresh seaweed takes place at a temperature in the range of 5 to 25 deg C.

3. The method according to claim 1, wherein pH during processing is not adjusted.

4. The method according to claim 1, wherein the cell wall degrading enzyme composition comprises one or more of cellulases, xylanases, beta-glucanases, alpha-amylases, beta-amylases, phytases, polygalacturonases and phospholipases.

5. The method according to claim 1, further comprising drying the liquid phase of step (iii) to obtain seaweed protein.

6. The method according to claim 5, wherein drying the liquid phase of step (iii) to obtain seaweed protein is by spray drying.

7. The method according to claim 1, wherein the pH during processing is between pH 5.5 and 7.5.

8. The method according to claim 1, wherein steps (i) to (iii) of processing of the seaweed takes place at a temperature in the range of 15 to 25 deg C.

9. The method of claim 1, wherein seaweed protein is obtained at a yield of 81% w/w, based on total protein in the seaweed.

* * * * *